(12) United States Patent
Lunin et al.

(10) Patent No.: US 6,316,004 B1
(45) Date of Patent: *Nov. 13, 2001

(54) CHIMERIC SOMATOSTATIN CONTAINING PROTEIN AND ENCODING DNA, PLASMIDS OF EXPRESSION, METHOD FOR PREPARING CHIMERIC PROTEIN, STRAIN-PRODUCERS, IMMUNOGENIC COMPOSITION, METHOD FOR INCREASING THE PRODUCTIVITY OF FARM ANIMALS

(75) Inventors: Vladimir Glebovich Lunin; Olga Vasileivna Sergienko; Marat-Vladimir Leonidovich Khodun; Leila Bakievna Bader; Vladimir Abramovich Karpov; Tomas Iosifovich Tikhonenko, all of Moscow (RU)

(73) Assignee: T. Tikhonenko, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/264,042

(22) Filed: Jun. 22, 1994

(30) Foreign Application Priority Data

Jun. 22, 1993 (RU) .................................................. 93031156
Jun. 22, 1993 (RU) .................................................. 93031157

(51) Int. Cl.[7] ........................ A61K 38/31; A61K 39/385; C12P 21/02; C07K 14/655
(52) U.S. Cl. .................................. 424/198.1; 424/185.1; 435/69.4; 530/311
(58) Field of Search .......................... 530/311; 435/69.4; 424/198.1, 185.1

(56) References Cited

U.S. PATENT DOCUMENTS 5,093,241 * 3/1992 Bennett et al. ...................... 435/69.4
5,506,120 * 4/1996 Yamamoto et al. ................. 435/69.7

OTHER PUBLICATIONS

Iwakura et al. "Dihydrofolate Reductase as a New Affinity Handle" J Biochem vol. III, No. 1, 1992, p. 37–45.*

Wootton et al. "The Q–linker A class of Interdomain Sequences found. . . " Protein Eng vol. 2 No. 7, 1989, p. 535–544.*

Spencer et al. "A Novel Approach to Growth Promotion Using. . ." Livestock Production Science 10:469–477, 1983.*

Spencer et al. "Increased Growth in Lambs following Immunization. . ." Animal Prod 32:376, 1981.*

"General Aspects of the Biology and Function of Somatostatin", Y.C. Patel, *Basic and Clinical Aspects of Neuroscience*, vol. 4, Somatostatin, pp. 1–16, (1992), C. Weil, ed. Springer–Verlag.

"Peptides Derived From Mammalian Prosomatostatin", Robert Benoit, *Somatostatin, Basic and Clinical Status*, S. Reichlin, ed., pp. 3–50, 121–136, 146–156, 169–182, 221–228, 267–274 (1987), Plenum Press, New York.

"Immunosuppresion of the Growth Hormone in the Organisms of Animals," from *Basics of Agricultural Biotechnology*, pp. 102–106, Muromstev, G.S., et al., (1990) (in Russian with English translation attached).

*Control and Manipulation of Animal Growth*, P.J. Buttery, et al., 1986, pp. 105–118, "The Neurophysiological Control of Growth".

*Livestock Production Science*, 12 (1985), pp. 31–46, G.S.G. Spencer "Hormonal Systems Regulating Growth. A Review".

*Science*, vol. 198, No. 4321, Dec. 9, 1977, pp. 1056–1063, "Expression in *Escherichia coli* of a Chemically Synthesized Gene for the Hormone Somatostatin".

* cited by examiner

Primary Examiner—Ponnathapura Achutamurthy
Assistant Examiner—Phuong T. Bui
(74) Attorney, Agent, or Firm—Townsend & Townsend & Crew LLP

(57) ABSTRACT

Chimeric polypeptides having the immunogenicity of somatostatin include an amino acid sequence of somatostatin-14 and a protein carrier. The sequence of somatostatin-14 is joined to the 3'-end of the protein carrier by a spacer (Sp)n, wherein Sp consists of an alkaline amino acid and an amino acid that provides a rigid expended chain-like β-structure, and n designates the number of blocks in the spacer. In a preferred embodiment, n is from 1 to 8 and the protein-carrier is chloramphenicol acetyl transferase (CAT).

13 Claims, 5 Drawing Sheets

CHIMERIC SOMATOSTATIN CONTAINING PROTEIN AND ENCODING DNA, PLASMIDS OF EXPRESSION, METHOD FOR PREPARING CHIMERIC PROTEIN, STRAIN-PRODUCERS, IMMUNOGENIC COMPOSITION, METHOD FOR INCREASING THE PRODUCTIVITY OF FARM ANIMALS

FIELD OF THE INVENTION

The present invention relates to the field of gene and protein engineering, in particular to the preparation of chimeric proteins, the desired component of which for one or another reason cannot be obtained in a free form by microbial synthesis, and also because of its small size only has the properties of a hapten, i.e., is capable of inducing the formation of antibodies only after being joined to high-molecular carriers. In particular, tetradecapeptide somatostatin-14 having an amino acid sequence corresponding to amino acid positions 233 to 246 in Seq. ID Nos. 1 and 2, and amino acid positions 242 to 255 in Seq. ID No. 3 relates to such a genus of oligopeptides. The use of a chimeric somatostatin-comprising protein in an immunogenic composition to increase the productivity of farm animals is also proposed.

BACKGROUND OF THE INVENTION

Acceleration of the growth of farm animals at a lower cost per 1 kg of weight gain is one of the main problems of stock raising. It is known that the productivity of farm animals can be increased by giving them somatostatin, some anabolic hormones or antibiotics. However, the high cost of somatostatin does not always make this method profitable, and furthermore, the use of hormonal preparations especially anabolic ones in the production of foodstuffs is not received with enthusiasm by the public. For these reasons somatotropic preparations have not yet found wide use in stock raising and anabolic hormones are prohibited in animal husbandry. However, it is possible to increase the concentration of endogenic anabolic factors by acting on their inhibitor—somatostatin, which has good prospects for use in agriculture and in medicine (Muromtsev G. S. et al., 1990, "Basics of agricultural biotechnology", Agropromizdat, Moscow; Reichlin S., ed., 1987, Somatostatin, Basic and Clinical Status, Plenum Press, New York, Weil C., ed., 1992, Basic and Clinical aspects of neuroscience, v. 4 Somatostatin, Springer-Verlag; Spencer G. S., 1985, Hormonal systems regulating Growth, Review, Livestock Production Science, 12, 31–46).

Somatostatin, a biologically active tetradecapeptide having the following amino acid sequence—AGCKNFFWKTFTSC, is produced in the hypothalamus and the gastrointestinal tract. The sequence of somatostatin-14 is highly conservative among vertebrata, while in mammals in general it does not have a specific species. Somatostatin has a strong inhibiting effect on a large number of hormones and related thereto functions of the organism: somatostatin, the thyrotrophic hormone, insulin, glucogen, secretin, gastrin, pepsin, maletin and a number of regulatory peptides. The wide range of action of somatostatin on the factors necessary for growth and utilization of food provides a good outlook for its use as a means for controlling the growth of animals, for reduction of expenditures on foodstuff, etc. Therefore, the autoimmune reaction to somatostatin, resulting in a reduction of the concentration of this peptide in the blood, and a result induction of anabolic factors and acceleration of the growth of the animals, is one of great interest. Active or passive immunization of animals, as a result of which antisomatostatin antibodies (Reichlin, 1987; Spencer, 1985; Baile C. A. et al.) The neurophysiological control of growth, In: Control and Manipulation of Animal Growth, Buttery P. J. et al., ed., 1986, Butterworths, London, pp. 105–118) appear in the blood, is used to reduce the concentration of endogenic somatostatin.

Somatostatin is a low-molecular protein-hapten, its half-life in the blood stream is several minutes. In view of this somatostatin conjugates with various proteins are used for immunization with somatostatin. It should be underlined that this approach makes it possible to obtain ecologically pure food products, since it does not include the use of any preparations of direct hormonal effect or antibiotics, but is based on small changes in the concentration of endogenous protein anabolic factors, characteristic for elite, highly-productive animals (Reichlin, 1987; Buttery et al., 1986).

A large number of studies have shown that animals immunized with somatostatin have an average daily weight gain of 10–20%, an appetite reduced by 9% and an 11% increase in the efficiency of food utilization. Wherein improved absorption of food components and a slower passage of food through the gastrointestinal tract with sluggish peristalsis is observed. Animals immunized with somatostatin, and also their offspring, have correct proportions, and the distribution of the weight of the animals between the muscles, bones and fat is the same as in the control (Reichlin, 1987). Immunization of gestated goats results in an increase in the weight of newly-born by 10% and an increase in milk yield.

However, the wide use of somatostatin-14, in particular, to stimulate the growth of animals by means of immuno-correction using antisomatostatin antibodies (Muromtsev G. S. et al. and Reichlin, 1987) is not possible because of its high price, since the main way to obtain somatostatin is by chemical synthesis (38 U.S.A. dollars for 1 mg of a somatostatin preparation, Sigma catalog, U.S. A., 1992), and this does not make it possible to realize this approach in practice from an economical point of view. The development of gene engineering methods has made it possible to prepare a number of protein and peptide hormones by synthesis in the cells of microorganisms. However, it is not possible to effect the direct microbial syntheses of somatostatin using recombinant DNA technology because of its small size (14 amino acid residues) (Itakura R. et al., 1977), "Expression in E. coli of a chemically synthesized gene of the hormone somatostatin", Science, 1986, 1056–1063). Several methods for obtaining somatostatin in the form of chimeric proteins with subsequent specific cleavage of the product of interest have been described (Itakura R. et al., 1977; Russian patent application No. 4921158/13 of Mar. 26, 1991).

The first research in respect of obtaining somatostatin-14 by use of gene engineering technology was conducted in 1977 by Itakura. The authors constructed a hybride gene on the basis of β-galactosidase E. coli, in the C'-end region of which a chemically synthesized sequence of somatostatin is engineered. Later, effective producers of chimeric proteins were created on the basis of that process with a sequence of somatostatin introduced into chimeric trpE, trpD and recA E. coli genes. The level of expression of chimeric proteins reached 15–30% of the total amount of proteins, while the output of the somatostatin approached the requirements of industrial production (Itakura R. et al.).

A recombinant plasmid DNA encoding somatostatin and a strain E. coli—a producer of somatostatin, are taught in Russian patent application No. 4921158/13 with priority from Mar. 26, 1991. The claimed plasmid determines the constitutive synthesis of a hybride protein of chloramphenicol acetyl transferase-somatostatin-14 under the control of its own promoter in cells of *E. coli* MKD3207 with a reduction of the level of degradation of anomalous proteins. However, the gene engineering constructions described above ensure the preparation of chimeric proteins, the immunogenic activity of which with respect to somatostatin is extremely low, and therefore these proteins are not yet being used in agriculture or medicine.

SUMMARY OF THE INVENTION

The present invention relates to chimeric immunogenic proteins including somatostatin-14, coupled with a protein-carrier through a spacer $(Sp)_n$ ensuring the positioning of the somatostatin on the surface of the carrier. Wherein, the number of monomeric proteins of the spacer (n) is preferably from 1 to 8, while the spacer (Sp) includes a sequence of amino acids consisting of an alkaline amino acid and amino acid ensuring a rigid β-structure, in particular, Lys-Pro or Arg-Pro. The invention relates to recombinant DNA molecules encoding the aforementioned chimeric proteins, to a process for preparing immunogenic chimeric proteins, and also to strains of *Escherichia coli* transformed by the aforementioned DNAs which are producers of these proteins. In accordance with the invention, the chimeric protein is the base of an immunogenic composition for improving the productivity of farm animals. The proposed system for immunization of animals with a composition including the aforementioned chimeric protein results in a stable increase in productivity, which is the result of the specific effect of antisomatostatin immunization and the unspecific effect of stimulation, which effect is caused by the immunization procedure itself.

DETAILED DESCRIPTION OF THE INVENTION

Engineering a recombinant molecule of DNA encoding a chimeric protein having immunogenic activity provides for the exposition of an antigenic determinant of interest on the surface of protein carriers. This is achieved by joining a chemically synthesized nucleotide sequence encoding an amino acid spacer $(Sp)_n$ connected to an area of a DNA encoding an antigenic determinant to the 3'-end of a gene of a protein-carrier through an adaptor.

The step of engineering a chimeric protein with a spacer and its subsequent synthesis is prospective to obtain antibodies to antigens of relatively small peptides, the microbial synthesis of which in a free form is difficult, while chemical synthesis is expensive: somatostatin, an epidermal growth factor, eucaryotic antibiotics and some natural and synthetic peptides. The invention relates to an increase in the meat and milk productivity of farm animals using recombinant somatostatin-comprising proteins. New immunogenic chimeric proteins are proposed including an amino acid spacer (Sp) consisting of an alkaline amino acid and an amino acid ensuring a rigid β-structure, in particular lysin and proline or arginine and proline, resulting in localization of somatostatin on the surface of a carrier, which ensures its high immunogenicity.

Preferably the number of monomeric blocks (n) in the spacer is form 1 to 8 depending on the structure of the protein-carrier and localization of the somatostatin.

Various proteins, including bacterial chloramphenicol acetyl transferase (CAT) with different kinds of deletions, β-galactosidases, dihydropholatreductases, hydrophobic synthetic polypeptides, etc. can be used as the carriers for somatostatin.

It is preferable that inactive chloramphenicol acetyl transferase without 10 C-end amino acids be used for large-scale synthesis of chimeric somatostatin-comprising proteins. Chimeric somatostatin-comprising protein with the aforementioned chloramphenicol acetyl transferase, obtained as a result of microbial syntheses, turned out to be hydrophobic. Both constitutive (in particular, its own promoter of chloramphenicol acetyl transferase in the construction $pC(Sp)_nS$) and inducible or quasi-inducible promoters (Tac, Lac, Trp, T5, CAT can be used to express a chimeric somatostatin-comprising protein. With small-scale microbial synthesis of a chimeric protein in fermenters of up to 100 1 wherein chloramphenicol acetyl transferase (CAT) is used, it is preferably that the CAT-promotor itself be used. With large-scale synthesis in fermenters of 0.05–1 $m^3$ and larger, and also when other proteins are used, it is preferable to use inducible or quasi-inducible promoters. It is most preferable to use inducible T5-Lac promoter with IPTC as the inductor or quasi-inducible CAT-promotor inhibited at the first half of microbial growth cycle by the presence of 0.5% glucose in the growth media.

Figure 1A:
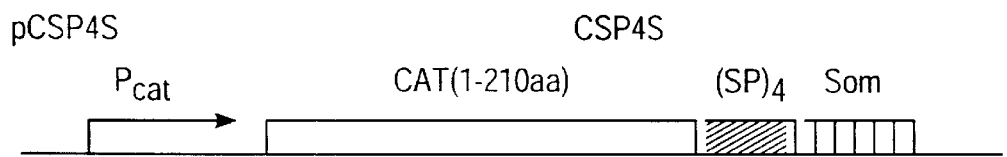
FIGS. 1A–1D are schematic drawings.
Figure 1B:
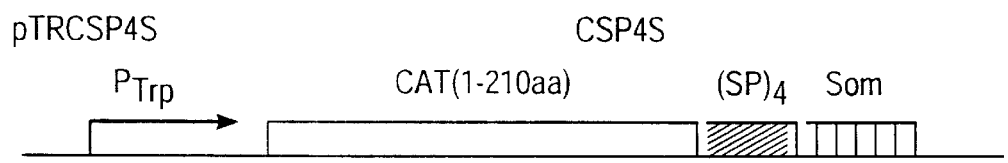
Figure 1C:
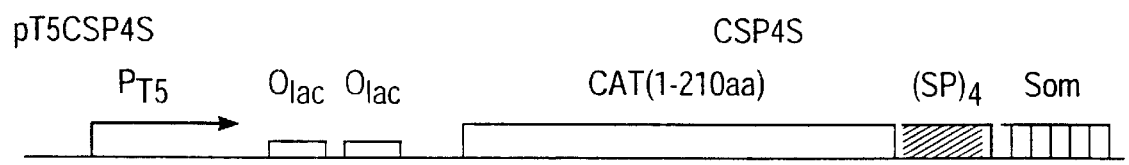
Figure 1D:
Figure 2:
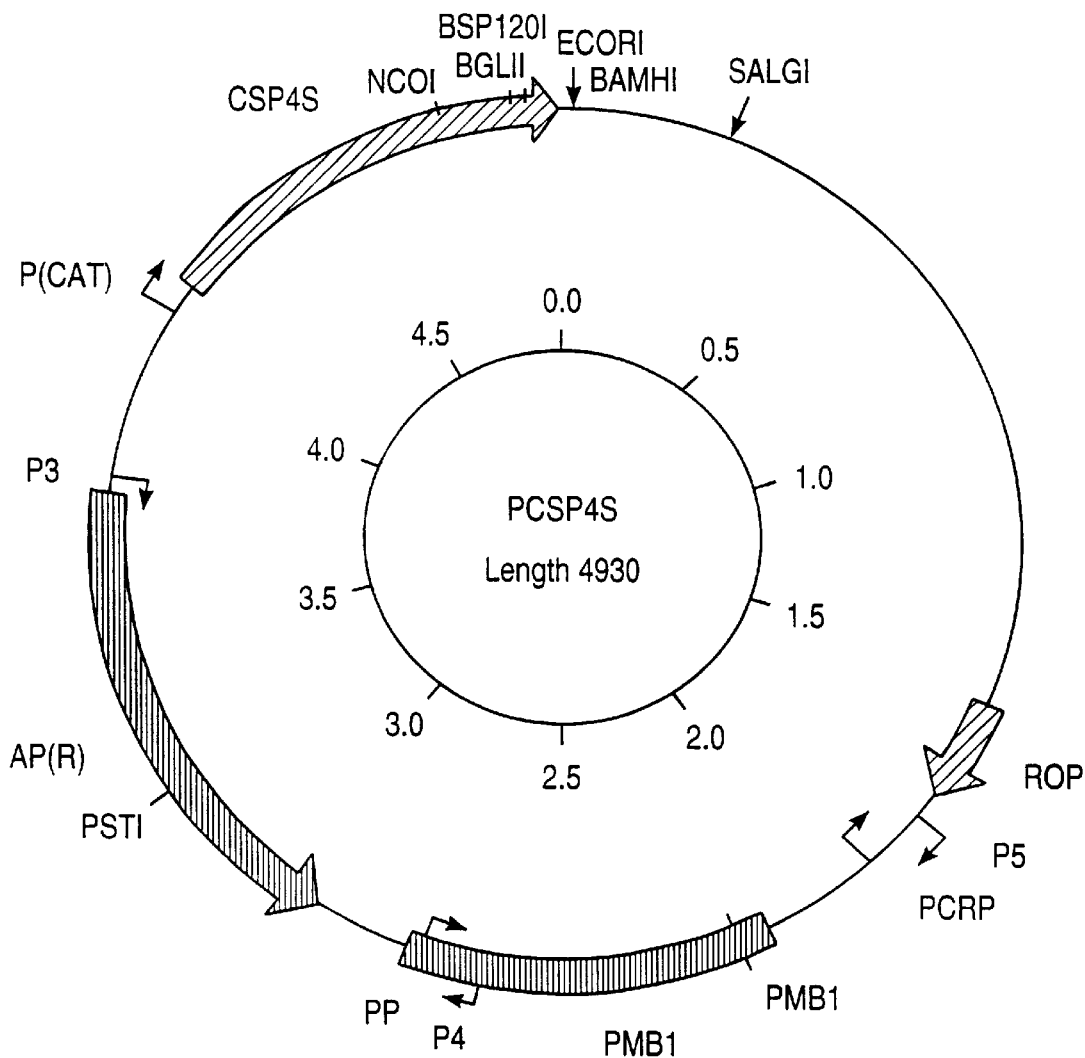
FIG. 2 shows a physical map of a pCsP4S plasmid.
Figure 3:
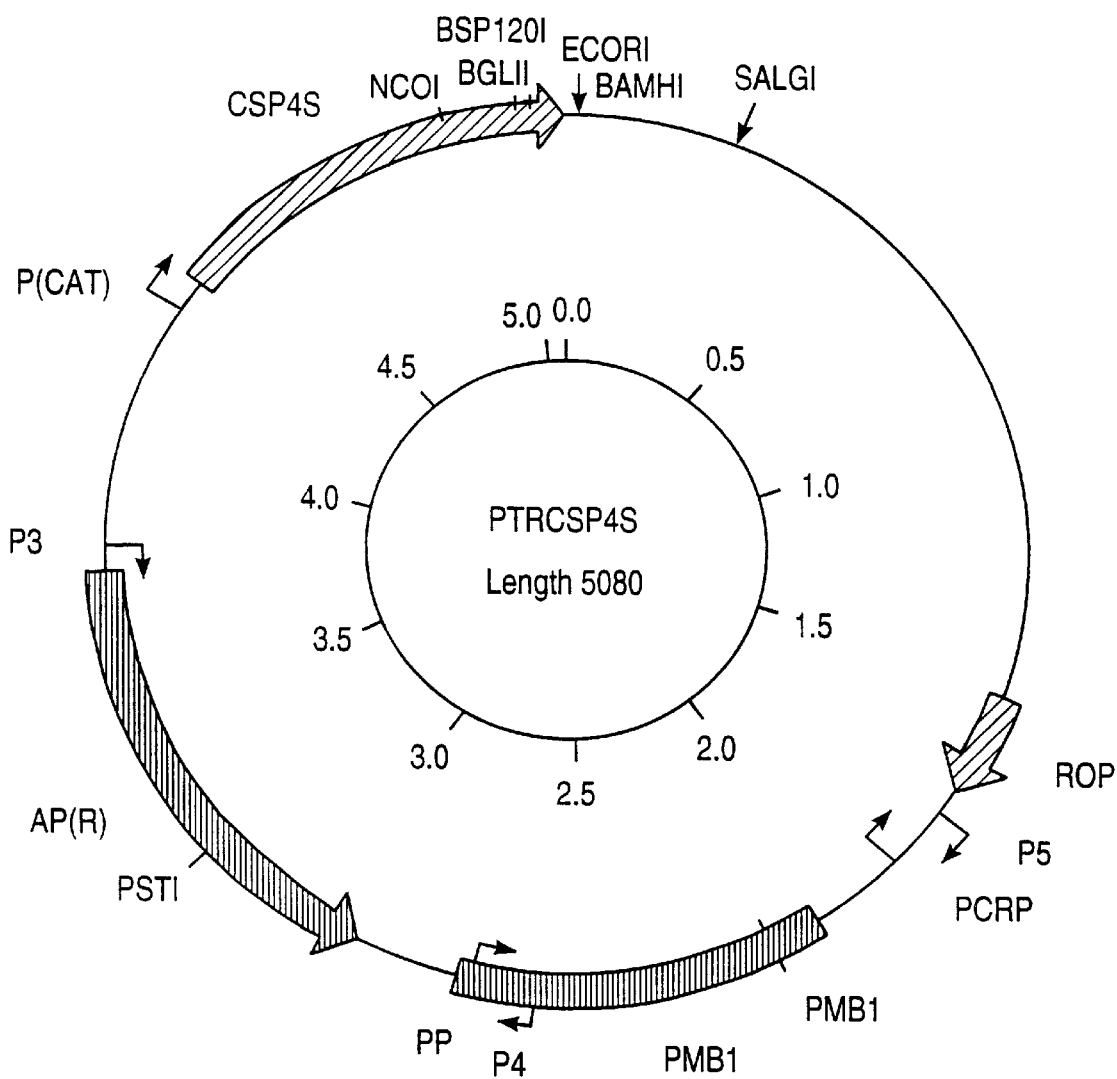
FIG. 3 shows a physical map of a pTRCSP4S plasmid.
Figure 4:
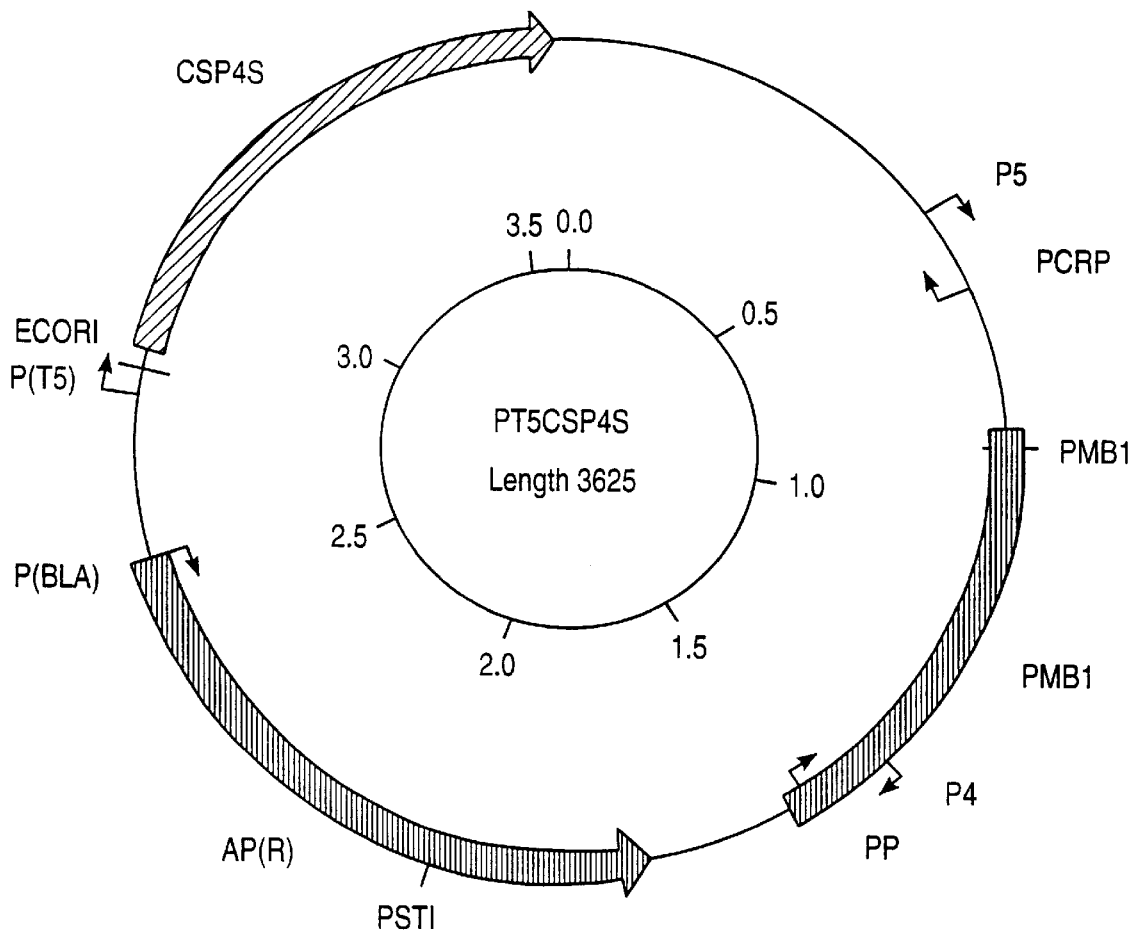
FIG. 4 shows a physical map of a pT5CSP4S plasmid.
Figure 5:
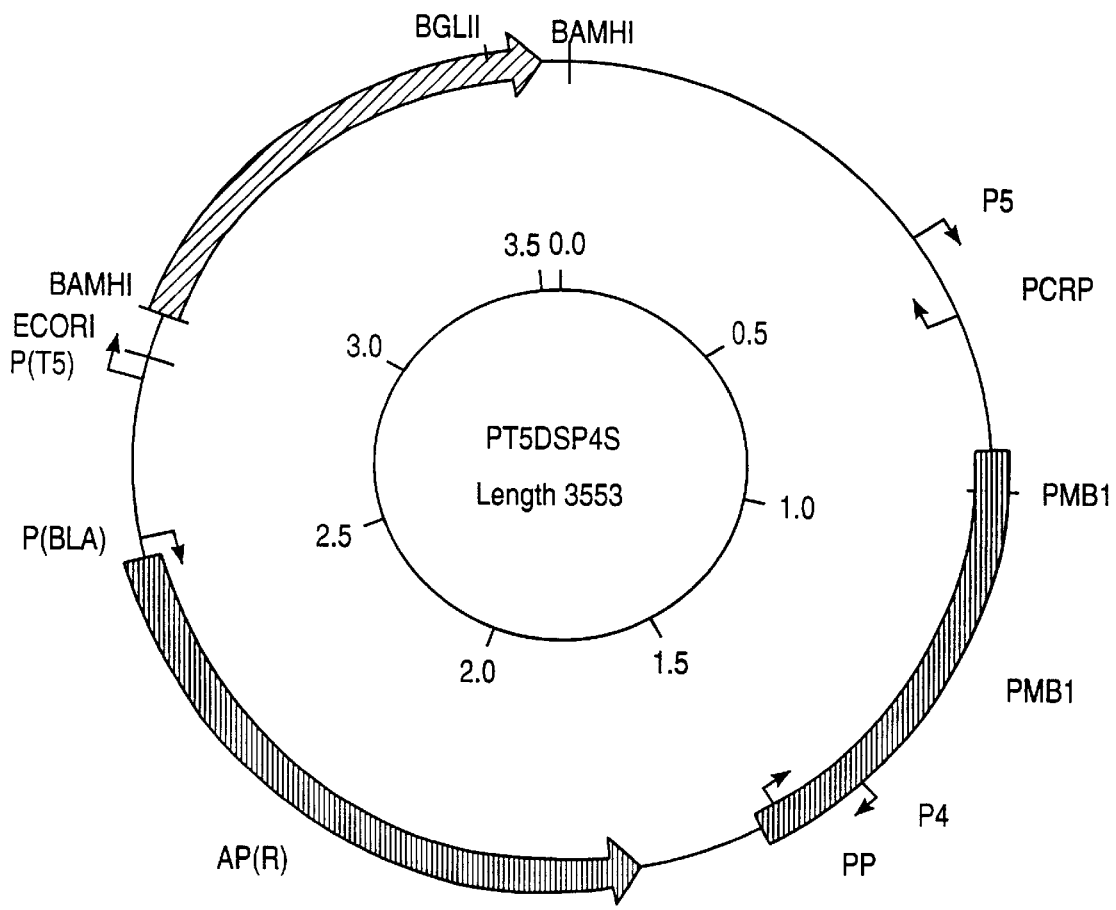
FIG. 5 shows a physical map of a pTDSP4S plasmid.

Recombinant plasmid DNAs ensuring expression of chimeric somatostatin-comprising proteins under the control of CAT, Trp, T5 promoters with CAT and DHFR proteins in *E. coli* cells used as the carriers are shown in FIGS. 1–5.

It should be noted that the aforementioned recombinant plasmid DNAs are only illustrations of the invention. The successful expression of chimeric DNA constructions according to the invention may be achieved, as stated above, with the use of other promoters and protein-carriers in suitable cells of microorganisms.

A $pC(Sp)_nS$ series of plasmids for expression of a chimeric somatostatin-comprising protein under the control of its own CAT promoter has been constructed using a CAT protein without 10 amino acid C-end as the carrier, wherein n is 1, 2, 4 and 8 (see examples 1, 2, and 3).

pTRCSP4S (FIG. 3) comprising promoter of tryptophane operon and pT5CSP4S (FIG. 4) with a phage T5 promoter (FIG. 4, example 6) are realizations of constructions in which expressions of DNA encoding chimeric immunogenic somatostatin-comprising proteins are under the control of inducible promoters.

One of the variants of the constructions in which proteins distinctive from chloramphenicol transferase are used as carriers is the recombinant plasmid DNA kpT5DSP4S (FIG. 5, example 7) comprising a gene dihydropholatreductase as the gene of the protein-carrier.

The method for preparing chimeric immunogenic somatostatin-comprising proteins includes cultivating cells of microorganisms. transformed by recombinant plasmids of DNA comprising sequences encoding the aforementioned proteins under conditions allowing their expression, and subsequent purification of the product of interest. Any suitable cells of microorganisms can be used as host cells, while any known plasmid systems suitable for expression in the selected host cells can be used as the expression vectors.

Purification of the product of interest is effected in accordance with known technology, including, for example, lysozyme lysis, differential centrifugation of inclusion bodies, sieve chromatography etc. Refolding procedure is conducted in guanidine chloride+urea at alkaline pH values followed by dialysis and lyophilization. The yield is about 0.4–0.69 of the purified protein per liter of bacterial suspension. Any person skilled in the art can select suitable methods for purification of the product of interest depending on the specific conditions.

In the preferable embodiments of the process for microbial synthesis of chimeric somatostatin containing proteins, according to the invention DNA constructions were used, as a result of the expression of which hydrophobic polypeptides were synthesized since hydrophilic chimerics are subjected to hydrolysis with bacterial proteases. Obtaining the product of interest in the form of hydrophobic inclusion bodies, on the one hand, isolates the recombinant proteins from the effect of the protease, and on the other hand, prevents possible undesirable effect of an excessive amount of an alien protein on the metabolism of cell-producers. The use of bacterial strain-producers, deficient in respect of protease, in particular $E.$ $coli$ lon-mutants also contributes to an increase in the output of chimeric proteins.

In accordance with the invention chimeric proteins produced by cells transformed by DNA recombinant plasmids interact with the antibodies to somatostatin-14, and when animals are immunized induce the synthesis of somatostatin-specific antibodies and immunocompetent cells specific to somatostatin. The amount of antisomatostatin antibodies in the serum of the immunized animals is determined by means of radioimmunoassay.

The contents of immunocompetent cells is determined by the method of biochemoluminescence after sensibilization with somatostatin (Khodum M. V. L., Ph.D., Thesis, "Study of physicochemical, immunological and biological properties of somatostatin-14 containing recombinant proteins and evaluating their possible use for stimulation of productivity of domestic animals", Moscow, Inst. Agricultural Biotechnology, 1994).

The molecular weight of the chimeric protein, determined by the method of electrophoresis in polyacrylamide gel under denaturating conditions, is 28 kDa.

In accordance with the invention the immunogenic composition for animals comprises a chimeric protein in an effective amount together with a emulgator or prolongator suitable for animals, such as for example, a solution of vitamins in vegetable oil, adjuvant, heated beeswax. Preferably, an incomplete standard Freund's adjuvant was used. The protein-carrier may be different. In particular it may be chloramphenicol acetyl transferase without 10C-terminal amino acids, or dihydropholatreductase, amino acid spacer $(Sp)_n$', where n is preferably from 1to 8 depending on the structure of the protein carrier, and somatostatin-14 with the sequence AGCKNPPWKTPTSC.

Wherein in the proposed variant the weight ratio of the purified chimeric somatostatin-comprising protein to the incomplete Freund's adjuvant is from 1:0.05 to 1:10, most preferably 1:1 or 1:2.

The purpose of the composition described above is to increase the productivity of farm animals. Wherein the process of increasing the productivity of farm animals comprises injecting the animals with a preparation comprising a chimeric immunogenic protein in accordance with the invention. The preparation is injected intramuscularly or subcutaneously, preferably from 3 to 5 times. Wherein the first three injections are preferably given at intervals of 10–14 days, and then two booster injections are additionally given at two-month intervals.

In special embodiments of the claimed process immunization of pregnant mothers is carried out approximately 40–50 days before giving birth so as to prevent lag-phase in the induction of antisomatostatin antibodies and immune-competent cells targeted at somatostatin in the newly-born when it is immunized. The doses depend on the type of animal, the mode of immunization, the preferable amount of the dose is 40–60 µg/kg of the weight of the animal.

It should be underlined that the increase in meat and milk productivities of all animals tested caused by antisomatostatin treatment does not accompany by the increase of feed consumption. In some cases antisomatostatin immunocorrection is accompanied by improving the quality of animal products (decrease of fat content).

Examples will now be given illustrating but not limiting the present invention.

EXAMPLE I (Seq. ID Nos. 1 and 2)

Assembly and molecular cloning of the nucleotide sequence of a spacer (Sp) Arg-Pro or Lys-Pro.

In the case of the spacer Arg-Pro oligonucleotides (2 sequences GATCTATGC and AATTGCATA forming an adaptor, and 2 sequences GATCTGGGCCCCGGCCGG and AATTCCGGCCGGGGCCCA forming a spacer) are synthesized by the amidic method in a solution in a PS 200 Cruachem synthesizer (England). Each of the chains of synthesized nucleotide is phosphorylated separately. The reaction is carried out in 10 mM of a Tris-HCl buffer, pH 7.5, comprising 10 mM of $MgCl_2$' 50 mM of dithiothreitol, 1 mM of ATF and 100 pM of oligonucleotide, one unit of the T4 phage polynucleotide kinase during one hour at 37° C. After the reaction is over the enzyme is inactivated by heating for 10 minutes at 65° C.

In order to obtain a hybride protein comprising a spacer Lys-Pro, a fragment encoding Arg-Pro is cut from a plasmid $pC(Sp)_n4S$ at BgIII-EcoRI sites, and a sequence of 36 nucleotides GATCCGGAAAACCGAACCGAAAC-CGAAACCCGGGG and GCCTTTTGGCTTTGGCTTTG-GCTTT GGGCCCTTAA corresponding to nucleotide positions 653 to 688 of Seq. ID No. 2 and their complementary nucleotides encoding spacer $(Lys-Pro)_4$ was inserted in its place. The length of the aforementioned sequence accordingly changed with degrees of polymerization n>4 or <4.

A recombinant plasmid pCCs of size 4920 bp (Russian patent application No. 4921168/13 of Mar. 26, 1991) is used to clone the spacer sequence Sp. This plasmid comprises a fragment of vector pBR325 of size 4860 bp with a gene of β-lactamase and a part of a modified gene of chloramphenicol acetyl transferase (CAT), to the 3'-end of which a synthetic gene of somatostatin-14 is linked through a synthetic linker with the size EcoRI and flanked at 5'-end with nucleotide sequence GG. This plasmid determines the constitutive or quasi-inducible synthesis of a hybride protein CAT-somatostatin-14 under the control of its own CAT promoter in cells of $E.$ $coli.$ Cloning of Sp is carried out in two stages. At first a derivative pCCs is obtained in which the site of restriction endonuclease EcoRi is replaced by the site BgIII.

1A. Molecular Cloning of a BgIII-EcoRI Adaptor 1 mg of the plasmid pCCs is incubated with restriction endonuclease EcoRI in a buffer of 50 pM of Tris-HCl, pH 7.5, 100 pM of NaCl, 7 pM of MgCl$_2$' 7 mM of β-mercaptoethanol at 36° C. for 1 hour. 50 pM of each phosphorylated oligonucleotide of the adaptor is added to 1 μg of linearized plasmid pCCs. Ligation of the mixtures of oligonucleotides and plasmid DNA is carried out in a buffer for kinase comprising 1 unit of the T4 phase ligase. Incubation is carried out a 12° C. during 16 hours. The ligated mixture of DNA and oligonucleotides is introduced by transformation into cells of *E. coli* HB101. Transformation is carried out using frozen cells, 5 fresh colonies are dispersed on a shaker in 1 ml of a SOB medium (2% tripton, 0.5% yeast extract, 10 mM of NaCl, 10 mM of MgCl$_2$, 10 mM of MgSO$_4$. 500 μl of a suspension of cells are introduced into 10 ml of a liquid culture medium SOB and are grown at 37° C. to a titer of 7×10$^7$ cells/ml. The cells are cooled on ice and centrifuged at 800 g during 15 minutes at 4° C., the supernatant is thoroughly removed, and the deposit is suspended in 3.3 ml of a buffer with rubidium chloride (100 mM of RbCl, 50 mM of MgCl$_2$, 30 mM of KAc, 10 mM of CaCl$_2$, 10 mM of glycerin, pH 6.8). The cells are kept on ice for 2 hours, centrifuged and the supernatant is thoroughly removed. It is resuspended in 800 μl of buffer comprising 10 mM of MOPS 10 mM of RbCl, 75 mM of CaCl$_2$, 15% glycerin and incubated for 15 minutes on ice. After that the aliquots of the final suspension are frozen in liquid nitrogen and used for transformation.

200 ml of the prepared suspension of cells are mixed with 5 ml of a solution of the ligated mixture and incubated for 30 minutes on ice, then for 90 seconds at 42° C., then again on ice for 2 minutes. 800 ml of the SOB medium are added and incubated with mild shaking at 37° C. during 60 minutes. A small portion of the suspension of cells is seeded on plates with agar, prepared on an SOB medium, comprising 1% of bactoagar and 50 mg/ml of ampicyline. 12 clones grown in the plate with ampicyline are arbitrarily selected, the plasmid DNA is separated using the alkaline method. After treatment of these plasmids with restriction endonucleases PstI and BgIII and electrophoresis in an agar gel, the plasmid of the desired construction is selected.

1B. Cloning an Sp Sequence

An initial plasmid pCCS and its modified derivative pCCS-BgIII are used to clone an Sp sequence (Arg-Pro or Lys-Pro). 3 mg of the plasmid pCCS are incubated with restriction endonucleases PstI and EcoRI, while plasmids pCCS-BgIII—with restriction endonuclease PstI and BgIII in a buffer and conditions as in example 1a. The fragments are divided by electrophoresis in an 0.8% agar gel. In the first case a large fragment (3296 bp) is cut from the gel and extracted from the gel with five volumes of 1.5M of NaCl. The supernatant obtained after centrifugating the suspension is treated with chloroform, the DNA is deposited with three volumes of ethyl alcohol. The DNA is dissolved in 10 ml of distilled water. In the second case a fragment of less molecular weight (1175 bp) is cut from the gel and treated in a similar manner. 50 pM of each phosphorylated oligonucleotide SP is added to 5 ml of the DNA preparation of each fragment. Ligation of the mixture of oligonucleotides and fragments of DNA is carried out in example 1a. Transformation of the ligated mixture and selection of the clones are carried out as in example 1a. An analysis of the sequence of a nucleotide insert was carried out initially with restriction mapping for the presence of restriction sites Bsp1201 and Eco521, and then the analysis of the nucleotide sequence was carried out by the Maxama-Gilbert method.

EXAMPLE 2

Polymerization of Sp

The nucleotide sequence Sp (Arg-Pro) includes restriction sites Bsp1201 and Eco521, the distinction of which is the presence of identical "sticky" ends with different flanking nucleotides in the first and sixth positions. Such an organization of sites makes it possible to conduct polymerization of the Sp, resulting in its size being increased. To do this 3 mg of the plasmid pCSpS in the first case are incubated with restriction endonucleases PstI and Bsp1201, and in the second case—with restriction endonuclease PstI and Eco521. A large fragment (3302 bp) was obtained from the products of the first hydrolysis, and a fragment of less molecular weight (1616 bp) from the products of the second hydrolysis. The procedure of elution, ligation, transformation, selection of clones was carried out as in example 1a. The DNA from the obtained clones was first analyzed by restriction mapping with endonucleases NcoI-Bsp1201 and NcoI-Eco521. The clones comprised dimer Sp and had an addition of 6 nucleotide pairs relative to the initial. The plasmid was designated pC(Sp)$_2$S. The polymerization procedure was carried out two more times, as a result of which clones were obtained with tetra- and octomers of Sp designated pC(Sp)$_4$S (pC(Arg-Pro)$_4$S: Seq. ID No. 1, pC(Lys-Pro)$_4$S: Seq. ID No. 2 and pC(Sp)$_B$S. These constructions are designated in general by (Sp)$_n$. In the examples described below plasmids with the number n=4, i.e., pC(Sp)$_4$S, were used in the majority of cases, although both pC(Sp)$_2$ and pC(Sp)$_B$ were also used. Polymerization of the spacer Lys-Pro was not carried out by this method. The necessary degree of polymerization was attained by chemical synthesis of the longer oligonucleotide (see example 1).

EXAMPLE 3

Use of recombinant plasmids of the pC(Sp)nS series to create strains-producers of *E. coli*.

Plasmids pC(Sp)$_n$S are brought by transformation into strains *E. coli* MKD3207 by the method described in example 1a, and strains-producers of hybride proteins are obtained.

The strain MKD3207 is characterized by the following features:

Cultural-morphological properties

The strain MKD3207 (derivative form *Escherichia coli* K12) is composed of gram-negative, slightly-mobile rods, under unfavorable conditions forming filaments. The strain grows well in a temperature range of from 30 to 42° C. on rich LB type mediums, and also on synthetic mediums with additives compensating auxotrophic mutation. On rich mediums the strain forms smooth colonies with even edges which in time mucify this being due to lon-mutation. Mucifying colonies does not take place at an incubation temperature of 40–42° C. The colonies are always mucific when grown on a synthetic medium with additives.

Genetic and physiological-biochemical features.

The stain MKD3207 has the following genetic markers: F$^-$, IacY, SupE, ga16, xy14, maI AI, arcH, Ris', Lon$^-$, apr 24, rpI. It is stable against streptomycin, does not ferment lactose, galactose, xylose and maltose. The strain grown on a synthetic medium with additives of glucose, arginine and histidine. The strain MKD3207 comprising the plasmid pC(Sp)$_n$S acquires resistance to ampicyline.

An analysis of the expression of genes encoding somatostatin as a part of hybride proteins is conducted in cells of *E. coli* MKD3207. The hybride genes in the expression vectors harbouring *E. coli* MKD3207 cells determine the constitutive sequence syntheses under the control of its own CAT promoters. The cells *E. coli* MKD3207, transformed by plasmids pC(Sp)$_1$S, pC(Sp)$_2$S, pC(Sp)$_4$S and pC(Sp)$_B$S, are grown in a 1 LB medium comprising ampicyline (50 mg/ml) to a density of $OD_{550}$ 2.0–2.5 at 37° C. during 18 hours. The original plasmid pCCS encoding chimeric protein CAT-somatostatin under the control of its own $P_{cat}$ is used as the control. A sediment of cells obtained from 1.5 ml of cell culture by centrifuging is then suspended in 200 ml of a buffer solution comprising 50 mM of Tris-HCl, pH 6.8, 10% glycerin, 2% SDS and 2% β-mercaptoethanol. The suspension is boiled for 5 minutes and analyzed by means of electrophoresis in 15% SDS-PAAG. The results show the presence of a dominating band having a molecular weight of 26.5 kDa for a chimeric protein with monomeric and dimeric copies of the spacer, 28 kDa for a tetrameric spacer and 30 kDa for an octomeric spacer sequence. The level of expression of hybride proteins with monomeric, dimeric and tetrameric spacer sequences is approximately equal and is 30% of the total bacterial proteins, and with an octomeric sequence —5%. The strain *Escherichia coli* MKD3207, transformed by plasmid $pC(sp)_4S$ was deposited in the All-Russian Collection of Cultures of Industrial Microorganisms under number B-6519.

EXAMPLE 4

Preparation of a hybride protein with a somatostatin sequence.

Cells of *E. coli* MKD3207 transformed by plasmid $pC(Sp)_4S$ are cultivated in a medium 1 LB as described in example 3 in a fermenter to a density $OD_{550}$ 4.0–5.0. The cells are deposited by centrifuging at 5000 g for 10 minutes. The sediment of the cells is suspended in 50 mM of tris—HCl, pH 8.0, comprising 50 mM of NaCl, 10 mM of EDTA calculated on the basis of 38 ml of a buffer for a biomass of one liter of cell culture. After suspending cells lysozyme is added to a final concentration of 100 mg/ml, Triton-X100 to a concentration of 0.1% and the suspension is incubated on ice. The cells are broken down by ultrasound. The sediment, including hydrophobic hybride protein in the form of inclusion bodies, collected by centrifuging at 12000 g and 4° C. for 10 minutes, is washed twice with a Triton containing buffer centrifuges and re-suspended in the original buffer without Triton. The aliquots are removed and analyzed by 15% SDS—PAAG electrophoresis. As a result of this purification procedure a preparation of hybride protein is obtained having a purification of more than 90% of the total proteins deposited.

Purification of chimeric proteins with other carriers is carried out according to the method described above.

This method of separation and purification of the hybride protein has been adapted for subsequent use as a preparation-stimulator in animal husbandry.

For immunological analysis a preparation of a protein obtained using the method described in example 4 is dissolved in 6 M of guanidinchloride, then dialyzated against 8 M of a urea solution in 10 mM of a carbonate buffer, pH 11, for two hours, and diluting the dialysis solution with 10 mM carbonate buffer, pH 11, twice, every two hours, the concentration of urea is brought to 1 M. Then dialysis is conducted against 10 mM of a phosphate buffer, pH 7.6, during 12 hours. The resulting solution is used as an antigen (adding to a reaction mixture in an excessive amount) in a concurrent RIA, conducted using a kit of the "Incstar" firm (USA). The preparation inhibits the binding of the $I^{125}$-labelled somatostatin with specific antisomatostatin antibodies (Table 1).

TABLE 1

Immunological analysis of a protein preparation

| | Sample | Binding percent |
|---|---|---|
| 1 | $B_0$ (sample without preparation being studied) | 100% |
| 2 | Background (sample without specific antibodies) | 16% |
| 3 | Control (sample with a carrier protein-chloramphenicol acetyl transferase | 98% |
| 4 | Experimental (sample with the CAT-SS-somatostatin) | 17% |

EXAMPLE 5

Obtaining a preparation for immunization

To purified protein isolated from hydrophobic inclusion bodies and dissolved in 0.2 M tris—HCl, buffer pH 8.0, comprising 6 M of guanidinchloride and 2 mM of EDTA, a 50-times molar excess of β-mercaptoethanol is added per 1 mole of S—S groups of chimeric protein and the solution is rapidly diluted in a 10-fold volume of buffer without guanidinchloride. The sedimented hybride protein is separated by centrifuging for 15 minutes of 12000 g and 4° C. Then the deposit is suspended in sterile distilled water and centrifugated, as described above, repeating the treatment twice. The final product is lyophilized for storage. Just before use the lyophilized preparation is re-suspended in a minimum volume of 10 mM of a phosphate buffer, pH 7.0, then equal volume of Freund's incomplete adjuvant is added and aqueous-oil suspension is homogenated under brief sonification. Immunization is conducted by intramuscular or subcutaneous injection of the suspension in the region of the neck or shoulder blade with a dose of 50 mg of chimeric protein for 1 kg of live weight. The injection is repeated three times at two-week intervals. Then, depending on the length of the incubation period, 1–2 more booster immunizations are given so that the productivity of the animals is increased to the desired level as they grow older.

EXAMPLE 6

Seq. ID Nos. 1 and 3

Engineering inducible producers of a chimeric protein with a somatostatin sequence.

Construction similar to $pC(Sp)_4S$ were created for use in a number of purposes including large-scale industrial synthesis of antisomatostatin chimeric proteins. To this end the hybride gene CAT-4S (CAT—210 amino acids, spacer Arg—Pro or Lys—Pro) and somatostatin was put under the control of a tryptophane operon (construction pTRCSP4S), $pTRC(Arg—Pro)_4S$: Seq. ID No. 1, a phage T5 promoter (construction pT5CSP-4S), $pT5C(Arg—Pro)_4S$: Seq ID No. 3, and a TAC-promoter (construction on pTACAP4S). The number of monomeric blocks of the spacer in the plasmid pTRCAP4S is as in the plasmid pC(Sp)4S equal to four. A plasmid having a size of 4994 bp comprises a ScaI—BamHI fragment of a plasmid vector pBR325 with a size of 4910 bp, including a part of a gene of tetracycline resistance with a BamHI site at the C-end, a gene of ampicyline resistance, a promoter region TAC of a plasmid pDR540, a part of a gene of chloramphenicol acetyl transferase with a half-site of ScaI at the 3'-end and an eliminated site of EcoRI, a SmaI—EcoRI fragment of a linker comprising a site of EcoRI and flanked with the 5'-end of a nucleotide sequence GGG of a half-site SmaI for joining to the 3'-end of a gene chloramphenicol acetyl transferase with site ScaI, a EcoRI*-BgIII fragment of an adaptor comprising a site of EcoRI*-BglII for connection to the 9 b.p. sequence of a spacer, a BglII—EcoRI spacer sequence of size 36 bp and a EcoRI—BamHI fragment of a synthetic gene of somatostatin with a "stop"-codon of size 54 bp. Genetic markers of this plasmid is a resistance to ampicyline. All three aforementioned constructions synthesized authentic chimeric proteins differing only in their transcription regulatory elements. The procedure of purifying and refolding was essentially similar to above described one. The properties of proteins and caused thereby physiological effects in the case of immunization of animals were also identical.

All three constructions are identical to pC(SP)$_4$S with the exception of the promoter region.

A strain comprising a plasmid pTACAP4S does not synthesize chimeric protein with a somatostatin sequence when grown on poor and enriched mediums. Induction of protein synthesis is effected by the addition of an β-indolilactylic acid inductor. The synthesis of a protein in a strain comprising plasmid pT5CAP4S is induced by isopropylthiogalactoside (IPTG) in a similar manner. The synthesis of protein in a strain comprising plasmid pTRCSP4S is induced by β-indolilacrylic acid. The amount of protein synthesized with inducible strains reached 40% of the total bacterial protein.

The molecular weight of the chimeric protein determined by electrophoretic mobility in a PAA-gel under denatured conditions is 28 kDa as in the case of pC(Sp)4S.

The chimeric protein interacts with antibodies against somatostatin-14 and in the case of immunization of animals induces the immuno-competent cells and somatostatin-specific antibodies.

EXAMPLE 7

Engineering a recombinant plasmid with a gene of mice dihydropholatreductase as the carrier.

A construction pT5DSP4S (FIG. 5) was created to study the physiological effects caused by a protein carrier (see below), in which construction modified mice dihydropholatreductase was used as the gene of a protein carrier. The region encoding the spacer Arg—Pro and somatostatin was used without changes. A hybride gene DSP4S was placed under the control of a phage promoter. The number of monomeric blocks of the spacer is, as in the plasmid pC(Sp)$_4$S, equal to four. Plasmids having size of 3553 bp comprise a fragment AatII—NdeI of a plasmid vector PBR322 having a size of 1992 bp, including a gene stable to ampicyline, a promoter region T5, a part of a gene dihydropholatreductase from the plasmid vector pQE16 with a half-site of restriction BglII at the 3'-end for connection with a sequence of a spacer, a BglII—EcoRI spacer sequence with a size of 36 bp and a EcoRI—BamHI fragment of synthetic gene of somatostatin with a "stop"-codon having a size of 54 bp, a gene of chloramphenicol acetyl transferase, genetic markers: resistance to ampicyline. The synthesized chimeric protein had similar physical-chemical properties. The procedure for purifying and preparing the preparation for immunization corresponded to a standard process. The physiological effects caused by the introduction of hybride protein with dihydropholatreductase were identical to those already described.

A strain comprising a plasmid pT5DSAP4S does not synthesize a chimeric protein with a somatostatin sequence when being grown on poor and enriched mediums. Induction of protein synthesis is effected when an inducer isopropylthiogalactoside (IPTG) is added. The amount of protein synthesized with inducible strains reaches 40% of the total bacterial protein.

The molecular weight of a chimeric protein determined by electrophoretic mobility in a PAA-gel under denatured conditions is 26 kDa.

The chimeric protein interacts with antibodies against somatostatin-14 and in the case of immunization of animals induces the synthesis of immuno-competent cells and somatostatin-specific antibodies.

EXAMPLE 8

Use of chimeric somatostatin-comprising proteins to increase productivity.

8a. Milk yield of dairy cattle

The preparation is injected into gestated heifers of the black breed, 24–25 months old, approximately 50 days before calving, the time of calving being determined by rectal test. The dose is 50 μg per 1 kg of live weight, the injections made in the region of the neck or shoulder blade and repeated three times at two-week intervals. Under these conditions, as shown above, antisomatostatin immuno-competent cells and corresponding antibodies appear in the blood, while toxicity of the preparation is not evident in immunized animals, no disturbances in the reproducing functions (abortions, still-born, deformities, etc.) are observed. Somatostatin-comprising proteins with chloramphenicol acetyl transferase (CAT) and dihydropholatreductase (DHFR) as carriers were used in the experiment.

In order to conduct analysis of the induction of specific antibodies against somatostatin, caused by immunization with the preparation, blood is taken from gestated cows and cows who have calved 7 days after the last injection, plasma is obtained and it is studied by radioimmunoassay using the procedure and a kit of the "Incstar" firm (USA). Specific binding of somatostatin is observed in preparations of plasma of the animals in the group being studied (Table 2).

TABLE 2

Induction of specific antibodies against somatostatin

| | Sample | Binding percent |
|---|---|---|
| 1 | B$_0$ (Sample without preparation being studied) | 100.00% |
| 2 | Background (sample without specific antibodies) | 11.80% |
| 3 | Control (sample with normal plasma) | 11.78% |
| 4 | Experiment (sample with plasma from a special experimental group to | 49.8% |

As is evident from the data in Table 3, in the case of immunized animals a substantial increase in milk yield was noted after calving right up to the 60th day of observation for cows immunized with chimeric protein with somatostatin. At the 14th–30th days this difference reached 21%–22% and then stayed at the level of 9–13%, deviations in the data did not exceed 1.5–3.0%. Booster injections of chimeric proteins given in the groups 3 and 5 provided additional increase in milk yield.

TABLE 3

Indexes of milk yields of cows after giving birth
in experimental and control groups (%)

| | | Days after calving | | | |
|---|---|---|---|---|---|
| | Groups of animals | 14 | 30 | 60 | 90 |
| 1 | Control group | 100 | 100 | 100 | 100 |
| 2. | Cows immunized three times before calving (carrier - CAT)[++] | 121 | 122 | 106 | 105 |
| 3. | Same with an additional injection on 50th day after calving | 121 | 122 | 111 | 121 |
| 4. | Cows immunized three times before calving (carrier - DHFR)[+++] | 109 | 121 | 108 | 107 |
| 5. | Same with an additional injection on 50th day after calving | 120 | 121 | 111 | 122 |

[++]Preparations of protein pC(Sp)$_4$S and pC(Sp)$_8$S were used.
[+++]Similar results were also obtained with immunization of milk cows with preparations pC(Sp)$_4$S.

As is evident from the data in Table 3, a substantial increase in the milk yield is observed in the case of three-time immunization on the 10th–20th day after giving birth. This does not depend on the type of protein-carrier (CAT or DHFR) used. The maximum milk yield is evident up to the 30th–40th day and then falls to 11% on the 60th–90th day, but this reduction can be prevented by an additional (fourth injection) on the 50th day after calving.

8b. Daily weight gains for calves born by immunized cows with additional immunization of the calves after birth In these experiments the gestated cows prior to giving birth were immunized three times as indicated in 8a, and the daily weight gain of the calves was measured after birth. In one of the groups the calves were not immunized in order to determine the effect of the immunization of the mothers on the calves. In another group the usual three-time immunization of the delivered calves was carried out at 10-day intervals, beginning with the 20th–30th day after calving.

It is evident from the data presented in Table 4 that immunization of gestated cows who have not yet given birth results in an increase in the daily weight gain of calves, the maximum value being 120–125% at the 30th–40th day after birth. Wherein, a similar dynamic weight gain is observed if immunization is made with chimeric proteins comprising CAT or DHFR as the carrier. This shows that there is no effect of the protein-carrier on the efficiency of the claimed chimeric proteins in respect of growth and the productivity of meat growth.

Then the daily weight gain fell to 110–111% at the 50th–60th day, but the usual three-time immunization of calves, beginning with the 20th–30th day after birth, not only prevented this reduction but also caused an additional increase in meat productivity to 135–137% with respect to the control.

Thus, the stimulating effects due to immunization of the mothers during the gestation period an immunization of calves can be summed ensuring maximum increase in the daily weight gains.

TABLE 4

Indexes of weight gains of calves born from immunized cows and
subjected to additional immunization after birth (% in respect of control)

| | Immunization of pregnant cows* protein-carrier | | Additional immunization of calves delivered by immunized cows protein-carrier | |
|---|---|---|---|---|
| Day after | CAT | DGFR | CAT | DGFR |
| 10 | 112 | 111 | 112 | 111 |
| 20 | 120 | 120 | 120 | 121 |
| 30 | 120 | 124 | 125 | 124 |
| 40 | 120 | 118 | 128 | 126 |
| 50 | 111 | 110 | 130 | 131 |
| 60 | 110 | 110 | 135 | 137 |

*Three-time immunization of calves on 20th–30th day after birth with 10 day interval.

8c. Productivity of swine

Sows of the large white breed are injected with a preparation comprising a chimeric protein suspended in Freund's incomplete adjuvant approximately 50 days before giving birth. The dose is 50 mg per 1 kg of the weight of the animal, injected intermuscularly in the region of the neck.

Immunization of the pig-mother is conducted three times at intervals of two weeks. The immunized animals do not exhibit manifestations indicating toxicity of the preparation, including disturbances of the reproducing functions (abortions, still-born, etc.). The indexes of piglet weight in the experimental group are 1.5 times greater than in the control group (Table 5). In order to maintain a greater meat productivity in piglets delivered by immunized sows, the piglets were immunized three times in accordance with the aforementioned schedule (with two-week intervals and a dose of 50 mg of chimeric protein per 1 kg of animal weight) (Table 6).

TABLE 5

Indexes of the productivity of pig-mothers in
experimental and control groups

| | Group of animals | Average weight of piglet 15 days after birth |
|---|---|---|
| 1. | Control (nonimmunized animals) | 5.10 ± 0.18 |
| 2. | Experimental group (immunized with somatostatin CAT chimeric protein) | 7.73 ± 0.43 |

TABLE 6

Indexes of meat productivity in piglets under
different modes of antisom immunization (%)*

| | Non-immunized pregnant sows | | Immunized pregnant sows | |
|---|---|---|---|---|
| Days after birth | Non-immunized piglets | Immunized piglets | Non-immunized piglets | Immunized piglets |
| 30 | 100 | 101 | 112 | 111 |
| 60 | 100 | 105 | 108 | 115 |
| 90 | 100 | 106 | 103 | 117 |
| 120 | 100 | 107 | 102 | 118 |

TABLE 6-continued

Indexes of meat productivity in piglets under different modes of antisom immunization (%)*

| Days | Non-immunized pregnant sows | | Immunized pregnant sows | |
|---|---|---|---|---|
| after birth | Non-immunized piglets | Immunized piglets | Non-immunized piglets | Immunized piglets |

*Percentage of weight increase in relation to figures in the first (control) column: non-immunized pregnant sows and non-immunized piglets taken as 100%.

EXAMPLE 9

Factors of stimulation of the productivity of animals subjected to antisomatostatin correction.

TABLE 7

Increase in milk yields and weight gains in the case of immunization with somatostatin-comprising chimeric proteins and protein carriers

| | Change in % after immunization with: | | |
|---|---|---|---|
| | CAT-somatostatin | protein-carrier | |
| Type of product* | chimera | CAT | DGFR |
| Milk yield (cows) | 120.0 | 115.0 | 116.0 |
| Weight gain (piglets) | 107.0 | 102.0 | 103.0 |
| Weight gain | 130.0 | 115.0 | 118.0 |

*Conditions of immunization with chimeric CAT-somatostatin on native CAT, as in examples 1 and 2, the result in % relative to a control nonimmunized group. The result of analysis on the 50th day after onset of immunization.

As is evident from the data of Table 7, together with a substantial increase in the meat and milk productivity of animals when they are immunized with chimeric protein with somatostatin, a sufficiently effective and statistically reliable increase in milk yield and weight gain is also evident when immunization is carried out with a protein-carrier. This stimulating effect may be related to the stimulation of the life activity and productivity of animals under the effect of the immunization procedure itself, independent of the character of the immunogen, which has been noted a number of times in scientific literature. However, in the majority of these studies it was not the individual preparations of purified proteins that were used, but rather different kinds of polyantigenic complexes of unidentified composition from cell extracts and biological liquids to mixtures of organic substances of the fluvial mud type, which precludes the possibility for unambiguous interpretation of the obtained results (Konishev V.A., 1976, Chemical nature and systematization of substances regulating the process of growth of animal tissue. Successes of modern biology, 81, 2, 258–273). Thus, the final effect of increasing the productivity of farm animals after immunization with somatostatin-comprising chimeric protein includes the result of the specific effect of antisomatostatin response and the unspecific effect of immunization with a carrier, wherein immunization with a protein-carrier, in spite of the lesser stimulating effect, may also be used independently in practice. At the same time contrary to somatostatin-containing chimeric proteins, carriers proteins can influence meat or milk productivity only directly in the immunized animals themselves and not in their progeny, when pregnant females were immunized (data not shown) stimulating effects caused by carrier proteins observed for shorter period of time comparatively to somatostatin-comprising chimeras.

Deposition of Biological Materials

Strain *E. coli* MKD3207 comprising the plasmid pC(Sp)$_4$S has been deposited in the Collection of Industrial Microorganisms, Moscow, with number VKPM-B-6519.

---

What is claimed is:

1. A chimeric polypeptide having the immunogenicity of somatostatin, including an amino acid sequence of somatostatin-14 and a protein carrier, wherein the sequence of somatostatin-14 is joined to the 3'-end of the protein carrier through a spacer $(Sp)_n$, where Sp consists of an alkaline amino acid and an amino acid providing a rigid β-structure, and n designates the number of blocks in the spacer, wherein the polypeptide is encoded by Seq. ID No. 1 or Seq. ID No. 2, wherein Sp is Arg—Pro or Lys—Pro, and wherein n=4.

2. The polypeptide of claim 1, wherein the protein-carrier is chloramphenicol acetyl transferase.

3. The polypeptide of claim 2, wherein the chloramphenicol acetyl transferase has a deletion 10 amino acids long at the C-end.

4. The polypeptide of claim 1, wherein the protein carrier is dihydrofolatereductase.

5. The polypeptide of claim 2, where said polypeptide is water insoluble.

6. An immunogenic composition comprising the chimeric polypeptide of claim 1 together with a pharmaceutically suitable adjuvant in an amount effective to elicit an immune response.

7. The composition of claim 6, wherein the adjuvant is Freund's incomplete adjuvant.

8. The composition of claim 7, wherein the weight ratio of purified chimeric somatostatin-comprising protein to incomplete Freund's adjuvant is from 1:0.5 to 1:10.

9. The composition of claim 8, wherein the polypeptide and adjuvant are in a ration of 1:1.

10. The polypeptide of claim 3 encoded by Seq. ID No. 1 wherein Sp is Arg—Pro and n=4.

11. The polypeptide of claim 3 encoded by Seq. ID No. 2 wherein Sp is Lys—Pro and n=4.

12. The chimeric polypeptide of claim 1 encoded by a recombinant plasmid and being expressed under the control of constitutive or inducible promoters in bacterial cells.

13. The chimeric polypeptide of claim 12 wherein said bacterial cells comprise protease deficient *E. coli* strains.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 741 base pairs
        (B) TYPE: nucleic acid
        (C) STRANDEDNESS: double
        (D) TOPOLOGY: unknown (xi) SEQUENCE DESCRIPTION: SEQ ID NO:1:

```
ATG GAG AAA AAA ATC ACT GGA TAT ACC ACC GTT GAT ATA TCC CAA        45
Met Glu Lys Lys Ile Thr Gly Tyr Thr Thr Val Asp Ile Ser Gln
1               5                   10                  15

TGG CAT CGT AAA GAA CAT TTT GAG GCA TTT CAG TCA GTT GCT CAA        90
Trp His Arg Lys Glu His Phe Glu Ala Phe Gln Ser Val Ala Gln
                20                  25                  30

TGT ACC TAT AAC CAG ACC GTT CAG CTG GAT ATT ACG GCC TTT TTA       135
Cys Thr Tyr Asn Gln Thr Val Gln Leu Asp Ile Thr Ala Phe Leu
                35                  40                  45
```

```
AAG ACC GTA AAG AAA AAT AAG CAC AAG TTT TAT CCG GCC TTT ATT         180
Lys Thr Val Lys Lys Asn Lys His Lys Phe Tyr Pro Ala Phe Ile
                50                  55                  60

CAC ATT CTT GCC CGC CTG ATG AAT GCT CAT CCG GAA TTG GTG CAA         225
His Ile Leu Ala Arg Leu Met Asn Ala His Pro Glu Leu Val Gln
                65                  70                  75

TTC CGT ATG GCA ATG AAA GAC GGT GAG CTG GTG ATA TGG GAT AGT         270
Phe Arg Met Ala Met Lys Asp Gly Glu Leu Val Ile Trp Asp Ser
                80                  85                  90

GTT CAC CCT TGT TAC ACC GTT TTC CAT GAG CAA ACT GAA ACG TTT         315
Val His Pro Cys Tyr Thr Val Phe His Glu Gln Thr Glu Thr Phe
                95                 100                 105

TCA TCG CTC TGG AGT GAA TAC CAC GAC GAT TTC CGG CAG TTT CTA         360
Ser Ser Leu Trp Ser Glu Tyr His Asp Asp Phe Arg Gln Phe Leu
               110                 115                 120

CAC ATA TAT TCG CAA GAT GTG GCG TGT TAC GGT GAA AAC CTG GCC         405
His Ile Tyr Ser Gln Asp Val Ala Cys Tyr Gly Glu Asn Leu Ala
               125                 130                 135

TAT TTC CCT AAA GGG TTT ATT GAG AAT ATG TTT TTC GTC TCA GCC         450
Tyr Phe Pro Lys Gly Phe Ile Glu Asn Met Phe Phe Val Ser Ala
               140                 145                 150

AAT CCC TGG GTG AGT TTC ACC AGT TTT GAT TTA AAC GTG GCC AAT         495
Asn Pro Trp Val Ser Phe Thr Ser Phe Asp Leu Asn Val Ala Asn
               155                 160                 165

ATG GAC AAC TTC TTC GCC CCC GTT TTC ACC ATG GGC AAA TAT TAT         540
Met Asp Asn Phe Phe Ala Pro Val Phe Thr Met Gly Lys Tyr Tyr
               170                 175                 180

ACG CAA GGC GAC AAG GTG CTG ATG CCG CTG GCG ATT CAG GTT CAT         585
Thr Gln Gly Asp Lys Val Leu Met Pro Leu Ala Ile Gln Val His
               185                 190                 195

CAT GCC GTT TGT GAT GGC TTC CAT GTC GGC AGA ATG CTT AAT GAA         630
His Ala Val Cys Asp Gly Phe His Val Gly Arg Met Leu Asn Glu
               200                 205                 210

TTA CAA CAG TGG GAA TTG CAT AGA TCT GGG CCC CGG CCC CGG CCC         675
Leu Gln Gln Trp Glu Leu His Arg Ser Gly Pro Arg Pro Arg Pro
               215                 220                 225

CGG CCC CGG CCG GAA TTC ATG GCT GGT TGC AAA AAC TTC TTC TGG         720
Arg Pro Arg Pro Glu Phe Met Ala Gly Cys Lys Asn Phe Phe Trp
               230                 235                 240

AAA ACC TTC ACG TCT TGC TAG                                         741
Lys Thr Phe Thr Ser Cys
               245

(2) INFORMATION FOR SEQ ID NO:2:

(i) SEQUENCE CHARACTERISTICS:
        (A) LENGTH: 741 base pairs
        (B) TYPE: nucleic acid
        (C) STRANDEDNESS: double
        (D) TOPOLOGY: unknown (xi) SEQUENCE DESCRIPTION: SEQ  ID NO:2:

ATG GAG AAA AAA ATC ACT GGA TAT ACC ACC GTT GAT ATA TCC CAA          45
Met Glu Lys Lys Ile Thr Gly Tyr Thr Thr Val Asp Ile Ser Gln
1                5                  10                  15

TGG CAT CGT AAA GAA CAT TTT GAG GCA TTT CAG TCA GTT GCT CAA          90
Trp His Arg Lys Glu His Phe Glu Ala Phe Gln Ser Val Ala Gln
                20                  25                  30

TGT ACC TAT AAC CAG ACC GTT CAG CTG GAT ATT ACG GCC TTT TTA         135
Cys Thr Tyr Asn Gln Thr Val Gln Leu Asp Ile Thr Ala Phe Leu
                35                  40                  45
```

```
AAG ACC GTA AAG AAA AAT AAG CAC AAG TTT TAT CCG GCC TTT ATT      180
Lys Thr Val Lys Lys Asn Lys His Lys Phe Tyr Pro Ala Phe Ile
             50                  55                  60

CAC ATT CTT GCC CGC CTG ATG AAT GCT CAT CCG GAA TTG GTG CAA      225
His Ile Leu Ala Arg Leu Met Asn Ala His Pro Glu Leu Val Gln
             65                  70                  75

TTC CGT ATG GCA ATG AAA GAC GGT GAG CTG GTG ATA TGG GAT AGT      270
Phe Arg Met Ala Met Lys Asp Gly Glu Leu Val Ile Trp Asp Ser
             80                  85                  90

GTT CAC CCT TGT TAC ACC GTT TTC CAT GAG CAA ACT GAA ACG TTT      315
Val His Pro Cys Tyr Thr Val Phe His Glu Gln Thr Glu Thr Phe
             95                 100                 105

TCA TCG CTC TGG AGT GAA TAC CAC GAC GAT TTC CGG CAG TTT CTA      360
Ser Ser Leu Trp Ser Glu Tyr His Asp Asp Phe Arg Gln Phe Leu
            110                 115                 120

CAC ATA TAT TCG CAA GAT GTG GCG TGT TAC GGT GAA AAC CTG GCC      405
His Ile Tyr Ser Gln Asp Val Ala Cys Tyr Gly Glu Asn Leu Ala
            125                 130                 135

TAT TTC CCT AAA GGG TTT ATT GAG AAT ATG TTT TTC GTC TCA GCC      450
Tyr Phe Pro Lys Gly Phe Ile Glu Asn Met Phe Phe Val Ser Ala
            140                 145                 150

AAT CCC TGG GTG AGT TTC ACC AGT TTT GAT TTA AAC GTG GCC AAT      495
Asn Pro Trp Val Ser Phe Thr Ser Phe Asp Leu Asn Val Ala Asn
            155                 160                 165

ATG GAC AAC TTC TTC GCC CCC GTT TTC ACC ATG GGC AAA TAT TAT      540
Met Asp Asn Phe Phe Ala Pro Val Phe Thr Met Gly Lys Tyr Tyr
            170                 175                 180

ACG CAA GGC GAC AAG GTG CTG ATG CCG CTG GCG ATT CAG GTT CAT      585
Thr Gln Gly Asp Lys Val Leu Met Pro Leu Ala Ile Gln Val His
            185                 190                 195

CAT GCC GTT TGT GAT GGC TTC CAT GTC GGC AGA ATG CTT AAT GAA      630
His Ala Val Cys Asp Gly Phe His Val Gly Arg Met Leu Asn Glu
            200                 205                 210

TTA CAA CAG TGG GAA TTG CAT AGA TCC GGA AAA CCG AAA CCG AAA      675
Leu Gln Gln Trp Glu Leu His Arg Ser Gly Lys Pro Lys Pro Lys
            215                 220                 225

CCG AAA CCC GGG GAA TTC ATG GCT GGT TGC AAA AAC TTC TTC TGG      720
Pro Lys Pro Gly Glu Phe Met Ala Gly Cys Lys Asn Phe Phe Trp
            230                 235                 240

AAA ACC TTC ACG TCT TGC TAG                                      741
Lys Thr Phe Thr Ser Cys
            245
```

(2) INFORMATION FOR SEQ ID NO:3:

(i) SEQUENCE CHARACTERISTICS:
        (A) LENGTH: 768 base pairs
        (B) TYPE: nucleic acid
        (C) STRANDEDNESS: double
        (D) TOPOLOGY: unknown (xi) SEQUENCE DESCRIPTION: SEQ ID NO:3:

```
ATG AGA GGA TCT ATG CAA TTC GGC GCC GGG GAG AAA AAA ATC ACT       45
Met Arg Gly Ser Met Gln Phe Gly Ala Gly Glu Lys Lys Ile Thr
 1               5                  10                  15

GGA TAT ACC ACC GTT GAT ATA TCC CAA TGG CAT CGT AAA GAA CAT       90
Gly Tyr Thr Thr Val Asp Ile Ser Gln Trp His Arg Lys Glu His
             20                  25                  30

TTT GAG GCA TTT CAG TCA GTT GCT CAA TGT ACC TAT AAC CAG ACC      135
Phe Glu Ala Phe Gln Ser Val Ala Gln Cys Thr Tyr Asn Gln Thr
             35                  40                  45
```

-continued

```
GTT CAG CTG GAT ATT ACG GCC TTT TTA AAG ACC GTA AAG AAA AAT         180
Val Gln Leu Asp Ile Thr Ala Phe Leu Lys Thr Val Lys Lys Asn
             50                  55                  60

AAG CAC AAG TTT TAT CCG GCC TTT ATT CAC ATT CTT GCC CGC CTG         225
Lys His Lys Phe Tyr Pro Ala Phe Ile His Ile Leu Ala Arg Leu
             65                  70                  75

ATG AAT GCT CAT CCG GAA TTG GTG CAA TTC CGT ATG GCA ATG AAA         270
Met Asn Ala His Pro Glu Leu Val Gln Phe Arg Met Ala Met Lys
             80                  85                  90

GAC GGT GAG CTG GTG ATA TGG GAT AGT GTT CAC CCT TGT TAC ACC         315
Asp Gly Glu Leu Val Ile Trp Asp Ser Val His Pro Cys Tyr Thr
             95                 100                 105

GTT TTC CAT GAG CAA ACT GAA ACG TTT TCA TCG CTC TGG AGT GAA         360
Val Phe His Glu Gln Thr Glu Thr Phe Ser Ser Leu Trp Ser Glu
            110                 115                 120

TAC CAC GAC GAT TTC CGG CAG TTT CTA CAC ATA TAT TCG CAA GAT         405
Tyr His Asp Asp Phe Arg Gln Phe Leu His Ile Tyr Ser Gln Asp
            125                 130                 135

GTG GCG TGT TAC GGT GAA AAC CTG GCC TAT TTC CCT AAA GGG TTT         450
Val Ala Cys Tyr Gly Glu Asn Leu Ala Tyr Phe Pro Lys Gly Phe
            140                 145                 150

ATT GAG AAT ATG TTT TTC GTC TCA GCC AAT CCC TGG GTG AGT TTC         495
Ile Glu Asn Met Phe Phe Val Ser Ala Asn Pro Trp Val Ser Phe
            155                 160                 165

ACC AGT TTT GAT TTA AAC GTG GCC AAT ATG GAC AAC TTC TTC GCC         540
Thr Ser Phe Asp Leu Asn Val Ala Asn Met Asp Asn Phe Phe Ala
            170                 175                 180

CCC GTT TTC ACC ATG GGC AAA TAT TAT ACG CAA GGC GAC AAG GTG         585
Pro Val Phe Thr Met Gly Lys Tyr Tyr Thr Gln Gly Asp Lys Val
            185                 190                 195

CTG ATG CCG CTG GCG ATT CAG GTT CAT CAT GCC GTT TGT GAT GGC         630
Leu Met Pro Leu Ala Ile Gln Val His His Ala Val Cys Asp Gly
            200                 205                 210

TTC CAT GTC GGC AGA ATG CTT AAT GAA TTA CAA CAG TGG GAA TTG         675
Phe His Val Gly Arg Met Leu Asn Glu Leu Gln Gln Trp Glu Leu
            215                 220                 225

CAT AGA TCT GGG CCC CGG CCC CGG CCC CGG CCC CGG CCG GAA TTC         720
His Arg Ser Gly Pro Arg Pro Arg Pro Arg Pro Arg Pro Glu Phe
            230                 235                 240

ATG GCT GGT TGC AAA AAC TTC TTC TGG AAA ACC TTC ACG TCT TGC         765
Met Ala Gly Cys Lys Asn Phe Phe Trp Lys Thr Phe Thr Ser Cys
            245                 250                 255

TAG                                                                  768
```